United States Patent [19]

Kis

[11] Patent Number: 4,995,271
[45] Date of Patent: Feb. 26, 1991

[54] APPARTAUS FOR DETERMINING THE PERMEABILITY OF A WEB TO AIR

[75] Inventor: Ludwig Kis, Puchenau, Austria

[73] Assignee: Textilmaschenenfabrik Dr. Ernst Fehrer Aktiengesellschaft, Leonding, Austria

[21] Appl. No.: 478,231

[22] Filed: Feb. 9, 1990

[30] Foreign Application Priority Data

Feb. 27, 1989 [AT] Austria .................................. 428/89

[51] Int. Cl.⁵ ............................................ G01N 15/08
[52] U.S. Cl. .......................................... 73/38; 73/37.7
[58] Field of Search ........................... 73/38, 37.7, 37.6

[56] References Cited

U.S. PATENT DOCUMENTS 3,218,844 11/1965 Kleist et al. ...................... 73/37.6 X

FOREIGN PATENT DOCUMENTS 2403748 8/1975 Fed. Rep. of Germany ....... 73/37.7

Primary Examiner—John Chapman
Assistant Examiner—Joseph W. Roskos
Attorney, Agent, or Firm—Kurt Kelman

[57] ABSTRACT

The testing head of an apparatus for determining the permeability of a web to air comprises two rotatable parallel contact rollers, which are mounted between two end walls and comprise a rubber-elastic sheath each, and two sealing belts, which are trained around said contact rollers at both ends thereof and adjacent to their outer edges are provided with a sealing lip, which contacts the adjacent end wall. An endless covering belt is trained around reversing pulleys so that a suction space which is provided between the contact rollers and serves to suck a stream of measuring air through the web is closed at the top.

7 Claims, 1 Drawing Sheet

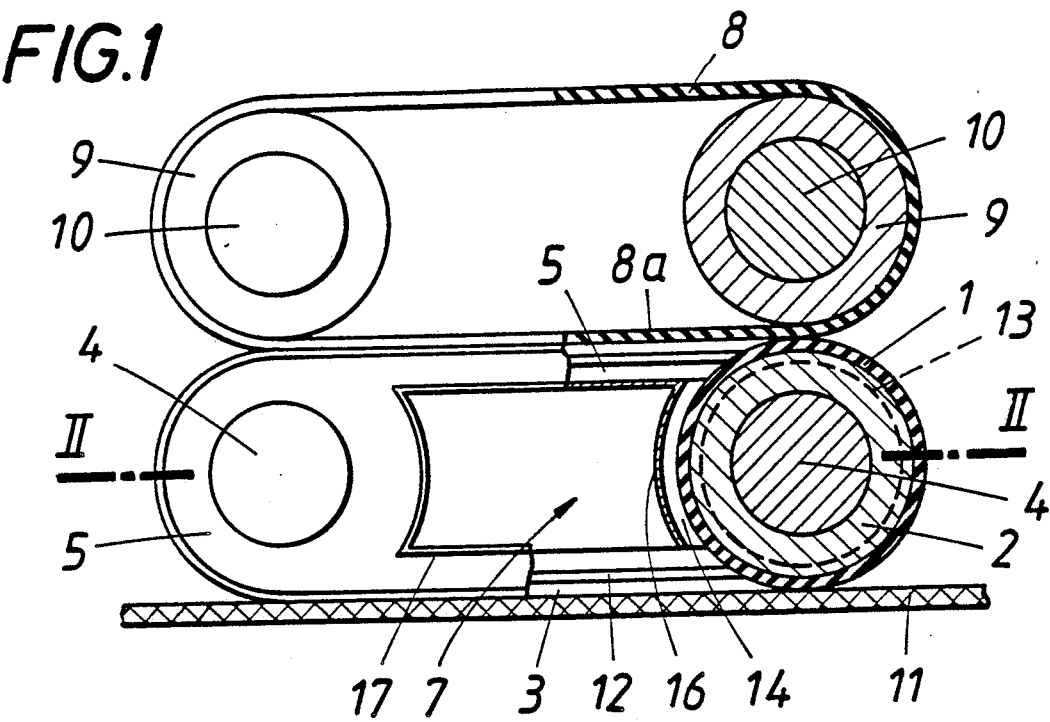
FIG.1
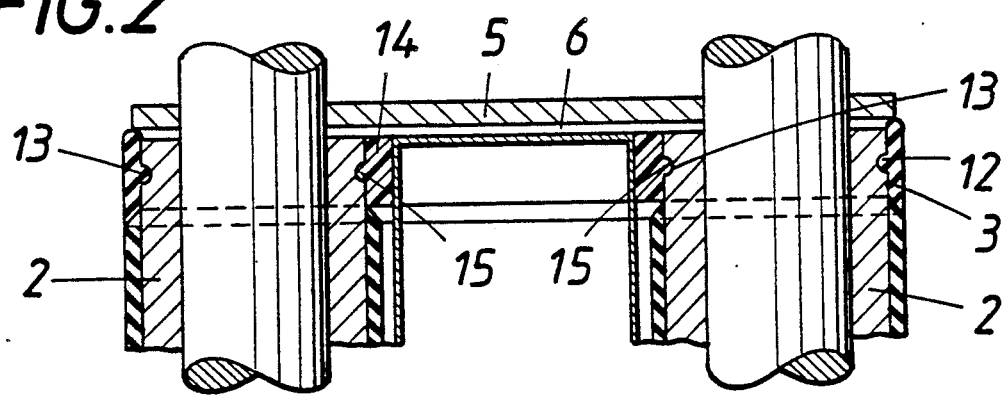
FIG.2
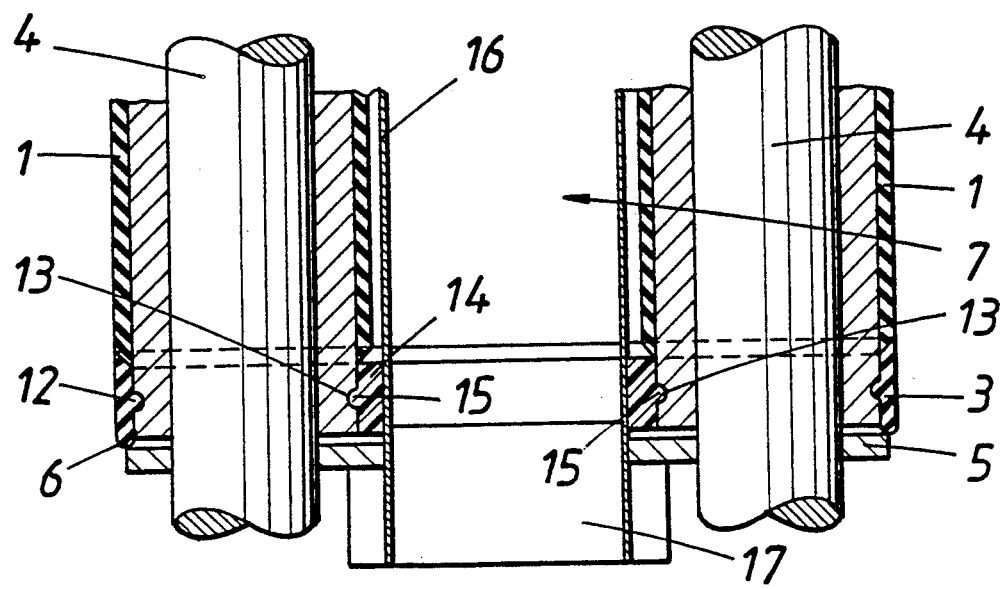

APPARTAUS FOR DETERMINING THE PERMEABILITY OF A WEB TO AIR

BACKGROUND OF THE INVENTION

1. Field of the Invention

This invention relates to an apparatus for determining the permeability of a web to air, comprising a testing head, which is adapted to be airtightly applied to the web and operable to suck or blow a stream of measuring air through the web, and a connecting line for a device for measuring the stream of measuring air.

2. Description of the Prior Art

For the determination of the permeability of sieves, woven fabrics or felts to air it is known to provide a testing head, which is applied to the web to be tested and is used to suck a stream of measuring air through the web under a predetermined suction pressure in a predetermined suction area and to measure said stream of air. For that purpose the testing head which defines the predetermined suction area must airtightly be applied to the web so that a suction of inleaked air will be prevented, which would adversely affect the result of the measurement. For that purpose the conventional testing heads have an annular seal, which defines the suction area and consists of rubber-elastic, soft material. Such seals have proved satisfactory with testing heads which do not move relative to the web. But difficulties will arise if such seal is used in a testing head which is moved relative to the web because a rapid wear is to be expected so that the required airtight joint between the suction opening of the testing head and the web can no longer be ensured. But for a continual inspection of webs for their permeability to air it would be desirable to provide a testing head which permits of a continuous movement of the web past the testing head.

SUMMARY OF THE INVENTION

For this reason it is an object of the invention to provide an apparatus which is of the kind described first hereinbefore and serves to determine the permeability of a web to air and is so improved that the testing head can airtightly be applied to a web moving relatively to said head whereas a premature wear of the sealing means need not be feared.

That object is accomplished in accordance with the invention in that the testing head comprises parallel rotatable contact rollers, which extend between two end walls and each of which has a rubber-elastic sheath, and two endless sealing belts, which are trained at opposite ends about said contact rollers and which in the region in which they are wrapped around the contact rollers constitute a gapless outside peripheral surfaces with the rubber-elastic sheaths of said rollers, whereas each sealing is provided at its outer edge with a sealing lip, which contacts the adjacent end wall, the opening which is defined by the contacting rollers and the two sealing belts on that side which is opposite to the contacting side is airtightly closed by and endless covering belt, which is trained around reversing pulleys, which are parallel to the contact rollers, and the connecting line for the measuring device extends from one end wall.

Because the suction area defined by the testing head is surrounded by a seal which is constituted by two contact rollers, which are provided each with an elastic sheath, and by two endless sealing belts, which are trained around and connect the contact rollers, it is possible to displace the testing head on the web transversely to the contact rollers without a risk of an occurrence of sliding friction, which would adversely affect the seal. This is possible because the contact rollers together with the sealing belts can roll on the web without an occurrence of a discontinuity in the closed sealing layer which defines the suction area. But to permit an air stream to be sucked through the web, which is moved relative to the testing head, the opening left between the contact rollers and the two sealing belts must be airtightly covered on that side which is opposite to the web. An occurrence of sliding friction between the moving contact rollers, which are interconnected by the sealing belts, and the covering, an endless covering belt which is trained around reversing pulleys is urged against the contact rollers and the sealing belts which connect the contact rollers so that a gapless seal is obtained between the elements which roll on each other. Because the sealing belts constitute sealing lips, which cooperate with the end walls, an airtightly closed suction space is formed between the contact rollers and defines a suction opening which can airtightly be joined to a web which moves relative to the testing head in the direction in which the contact rollers roll on the web. In that case the stream of sucked measuring air can be supplied via a connecting line, which is connected to an end wall, to a suitable measuring device for determining the permeability of the web to air. Such testing head can be used not only for sucking a stream of measuring air but may also be used to blow an air stream through the web although more favorable sealing conditions will obviously be obtained if a subatmospheric pressure is maintained in the testing head.

For the sealing of the contacting surface of the testing head relative to the web it is essential that the sealing belts and the rubber-elastic sheaths of the contact rollers constitute a gapless sealing surface in the region in which the sealing belts are wrapped around the contact rollers. For this reason, care must be taken to prevent a wandering of the sealing belts relative to the contact rollers. For that purpose each sealing belt has desirably at least one guide rib, which extends into a peripheral groove formed in each contact roller. The provision of the peripheral groove in each contact roller also permits a simple arrangement of spacers, which have guide ribs extending into the peripheral grooves of the contact rollers and are thus held against an axial displacement.

If the two spacers are connected by a suction or blasting inert, which is open toward the contacted surface and is connected to the connecting line, the suction or blasting insert and the two spacers will constitute in a simple manner a carrying structure, to which the contact rollers provided with the sealing belts can be connected in a desirable manner.

BRIEF DESCRIPTION OF THE DRAWING

FIG. 1 is a simplified side elevation, which is partly torn open and shows a testing head of an apparatus in accordance with the invention for determining the permeability of a web to air.

FIG. 2 shows that testing head in a sectional view taken on line II—II in FIG. 1.

DETAILED DESCRIPTION OF THE PREFERRED EMBODIMENT

The invention is illustrated by way of example on the drawing.

In the embodiment shown by way of example the testing head essentially comprises two parallel contact rollers 2, which are laterally spaced apart and each of which has a rubber-elastic sheath 1. Adjacent to the two ends of said rollers, two endless sealing belts 3 are trained around the contact rollers 2 and in the region in which the contact rollers are wrapped by the sealing belts 3 the latter constitute a gapless outside peripheral surface together with the rubber-elastic sheath 1, as is particularly apparent from FIG. 2. The axles 4 of the contact rollers 2 are held in end walls 5, which are disposed within the outer contour line of the sealing belts 3 and which cooperate with a sealing lip 6, which is formed on each sealing belt 3 and protrudes in an endwise direction so that the end walls 5 airtightly contact the sealing belts 3 throughout their periphery. Because the axles 4 of the contact rollers 2 extend also airtightly through the end walls 5, the suction space 7 between the contact rollers 2 is airtightly sealed at its ends. But that suction space 7 must also airtightly be sealed on that side which is opposite to the contacting side. This is accomplished by the provision of an endless covering belt 8, which is trained around reversing pulleys 9, which have axles 10, which are parallel to the axles 4 of the contact rollers 2 and just as the axles 4 of the contact rollers 2 are mounted in a housing, which is not shown, so that that course 8a of the covering belt which faces the suction space 7 can be forced against the contact rollers 2 and the sealing belts 3 in right contact therewith.

When that testing head is applied to the web 11, a seal which is closed in itself is obtained in the region between the web 11 and the testing head along a generatrix of each contact rollers 2 and along the sealing belts 3 which connect said generatrices and a similar seal is provided between the course 8a of the covering belt, on the one hand, and the contact rollers and the sealing belts 3, on the other hand. As said seals will be maintained also when the testing head is rolled on the web 11, the permeability of a continuously moving web to air can readily be determined.

It is apparent from FIG. 2 that each sealing belt 3 is provided with a guide rib 12, which extends into a peripheral groove 13 formed in each contact roller 2 so that an axial wandering of the sealing belts 3 will be prevented. Said peripheral grooves 13 serve also for an axial fixation of spacers 14, which are disposed between the contact rollers 2 and have guide ribs 15, which extend into the peripheral grooves 13 of the contact rollers 2. A simple and stable unit of construction is obtained because said spacers 14 are axially connected by a suction insert 16, which is connected to a connecting line 17, which extends airtightly through an end wall 5. As indicated hereinabove, connecting line 17 could supply air under pressure to blow the air through web 11 into sealed space 7, instead of sucking air through the web.

I claim:

1. In an apparatus for determining the permeability of a web to air, comprising
  a testing head, which is adapted to be applied to a web in airtight contact therewith and is operable to pass a stream of measuring air through said web, and
  a connecting line connected to said testing head and adapted to be connected to a measuring device for measuring said measuring air stream,
  the improvement residing in that
  said testing head comprises two laterally spaced apart end walls,
  two laterally spaced apart, parallel contact rollers extend between and are rotatably mounted in said end walls,
  each of said contact rollers is provided on its periphery with a rubber-elastic sheath and has to mutually opposite end portions axially protruding from said sheath,
  two endless sealing belts are provided, each of which has two wrapping portions, which are trained around corresponding ones of said end portions of said contact rollers and closely adjoin said sheaths, whereby said wrapping portions and said sheath constitute a gapless peripheral surface portion on each of said contact rollers,
  each of said sealing belts has an axially outer edge portion, which axially protrudes from said contact rollers and constitutes a sealing lip in sealing contact with the adjacent one of said end walls,
  said contacting rollers and said sealing belts define between them an air-guiding space and have a contacting side adapted to contact said web and an outer side opposite to said contacting side,
  two laterally spaced apart reversing pulleys, which are parallel to said contact rollers, are disposed on said outer side of said contact rollers,
  an endless covering belt is trained around said reversing pulleys and in sealing contact with said contact rollers and said sealing belts on said outer side thereof to seal said air-guiding space on said outer side, and
  said connecting line extends from one of said end walls and communicates with said air-guiding space.

2. The improvement set forth in claim 1, wherein said testing head is operable to suck said measuring air stream through said web.

3. The improvement set forth in claim 1, wherein said testing head is adapted to blow said measuring air stream through said web.

4. The improvement set forth in claim 1, wherein
  each of said contact rollers is formed in each of said end portions with a peripheral groove and
  each of said sealing belts has an inside surface formed with a longitudinally extending guide rib extending into said peripheral grooves of corresponding ones of said end portions.

5. The improvement set forth in claim 4, wherein
  a spacer is provided adjacent to each of said end portions of said contact rollers on that side thereof which is opposite to said wrapping portion of the adjacent one of said sealing belts and
  said spacer is formed with a guide rib extending into said peripheral groove of the adjacent one of said end portions of said contact rollers.

6. The improvement set forth in claim 5, wherein
  an air-guiding insert is disposed in said air-guiding space between said spacers and is connected to said spacers and is open on said contacting side of said contact rollers and sealing belts.

7. The improvement set forth in claim 6, wherein said air-guiding insert consists of a suction insert.

* * * * *